(12) United States Patent
Luneau et al.

(10) Patent No.: US 9,596,981 B2
(45) Date of Patent: Mar. 21, 2017

(54) CAVITY EXPLORATION WITH AN IMAGE SENSOR

(75) Inventors: Dominique Luneau, Chilly (FR); Paul Varillon, Grenoble (FR)

(73) Assignee: STMicroelectronics S.A., Montrouge (FR)

( * ) Notice: Subject to any disclaimer, the term of this patent is extended or adjusted under 35 U.S.C. 154(b) by 2812 days.

(21) Appl. No.: 12/117,646

(22) Filed: May 8, 2008

(65) Prior Publication Data

US 2008/0277673 A1    Nov. 13, 2008

(30) Foreign Application Priority Data

May 10, 2007   (FR) .................................... 07 03344
May 10, 2007   (FR) .................................... 07 03345

(51) Int. Cl.
| | | |
|---|---|---|
| *A61B 1/005* | (2006.01) | |
| *H04N 7/18* | (2006.01) | |
| *A61B 1/05* | (2006.01) | |
| *G02B 23/24* | (2006.01) | |
| *H04N 5/225* | (2006.01) | |
| *A61B 1/00* | (2006.01) | |

(Continued)

(52) U.S. Cl.
CPC .............. *A61B 1/05* (2013.01); *A61B 1/0008* (2013.01); *A61B 1/0051* (2013.01); *A61B 1/00114* (2013.01); *A61B 1/00181* (2013.01); *G02B 23/2423* (2013.01); *H04N 5/2251* (2013.01); *A61B 1/0011* (2013.01); *A61B 1/041* (2013.01); *A61B 1/06* (2013.01); *H04N 2005/2255* (2013.01)

(58) Field of Classification Search
CPC ....... A61B 1/041; A61B 1/011; A61B 1/0014; H04N 2005/2255
USPC ....... 600/179; 396/529; 348/68, 340; 385/14
See application file for complete search history.

(56) References Cited

U.S. PATENT DOCUMENTS

| | | | | |
|---|---|---|---|---|
| 3,975,579 A | * | 8/1976 | Davis ................... | H01B 17/308 174/153 R |
| 4,269,467 A | * | 5/1981 | Hughes .................. | H01R 13/33 29/883 |

(Continued)

FOREIGN PATENT DOCUMENTS

| | | |
|---|---|---|
| EP | 1 400 214 A2 | 3/2004 |
| EP | 1400214 A2 | 3/2004 |

(Continued)

*Primary Examiner* — Anthony Mejia
*Assistant Examiner* — Michael A Chambers
(74) *Attorney, Agent, or Firm* — Seed IP Law Group LLP (57) ABSTRACT

A head of a cavity exploration device, with an integrated circuit support which has first and second surfaces and a plurality of through-holes associated with corresponding first and second conducting pads positioned on the respective first and second surfaces of the integrated circuit support, a respective conducting micro-cable is placed in the through-hole, with this micro-cable having a portion which is uninsulated for a length greater than or equal to the thickness of the support. The micro-cable is soldered to the associated first and second conducting pads. Next the micro-cable is glued to the first and second associated conducting pads. The micro-cable is molded in first and second resin layers onto the respective first and second conducting pads, with the resin layers covering the uninsulated portion of the micro-cable.

12 Claims, 5 Drawing Sheets

(51) Int. Cl.
*A61B 1/04* (2006.01)
*A61B 1/06* (2006.01)

(56) References Cited

U.S. PATENT DOCUMENTS

| | | | | |
|---|---|---|---|---|
| 4,803,562 A * | 2/1989 | Eino | H04N 5/23203 | 323/223 |
| 4,809,680 A * | 3/1989 | Yabe | A61B 1/05 | 348/65 |
| 4,832,003 A * | 5/1989 | Yabe | A61B 1/051 | 348/65 |
| 4,845,555 A * | 7/1989 | Yabe | H04N 5/23203 | 348/72 |
| 4,868,644 A * | 9/1989 | Yabe | A61B 1/0052 | 348/76 |
| 4,918,521 A * | 4/1990 | Yabe | A61B 1/00179 | 348/373 |
| 5,021,888 A | 6/1991 | Kondou et al. | | |
| 5,055,068 A * | 10/1991 | Machura | H01R 24/50 | 439/581 |
| 5,220,198 A * | 6/1993 | Tsuji | A61B 1/05 | 257/680 |
| 5,438,478 A * | 8/1995 | Kondo | H01L 23/4334 | 174/260 |
| 5,800,341 A | 9/1998 | McKenna et al. | | |
| 5,966,168 A * | 10/1999 | Miyazaki | A61B 1/00096 | 348/68 |
| 5,986,693 A * | 11/1999 | Adair | A61B 1/00135 | 257/E25.032 |
| 6,160,771 A * | 12/2000 | Kawano | G11B 7/22 | 369/44.14 |
| 6,184,923 B1 * | 2/2001 | Miyazaki | A61B 1/00096 | 348/75 |
| 6,547,721 B1 * | 4/2003 | Hiroya | A61B 1/121 | 600/109 |
| 6,652,451 B2 * | 11/2003 | Murata | G02B 23/2484 | 348/65 |
| 6,743,656 B2 * | 6/2004 | Orcutt | B81B 7/007 | 257/E23.193 |
| 6,749,345 B1 * | 6/2004 | Gee | G02B 6/421 | 385/75 |
| 6,928,864 B1 * | 8/2005 | Henry | E21B 17/023 | 166/54.1 |
| 6,939,295 B2 * | 9/2005 | Yokoi | A61B 1/041 | 600/160 |
| 7,129,473 B2 * | 10/2006 | Ishihara | A61B 1/0008 | 250/234 |
| 7,304,287 B2 * | 12/2007 | Mabuchi | H01L 27/14609 | 250/208.1 |
| 7,306,377 B2 * | 12/2007 | Ellison | G02B 6/4246 | 385/14 |
| 7,427,747 B2 * | 9/2008 | Ishihara | A61B 1/0008 | 250/205 |
| 7,473,218 B2 * | 1/2009 | Segawa | A61B 1/0011 | 348/340 |
| 7,560,802 B2 * | 7/2009 | Kalvesten | B81B 7/0006 | 257/621 |
| 7,691,056 B2 * | 4/2010 | Hirata | A61B 1/00096 | 600/117 |
| 7,785,024 B2 * | 8/2010 | Fujimori | G03B 17/02 | 348/340 |
| 7,846,107 B2 * | 12/2010 | Hoffman | A61B 10/06 | 600/561 |
| 7,850,678 B2 * | 12/2010 | Toyama | A61B 1/00071 | 600/101 |
| 2002/0043883 A1 * | 4/2002 | Shimizu | H01R 13/405 | 310/71 |
| 2002/0126204 A1 * | 9/2002 | Takeshige | A61B 1/00009 | 348/74 |
| 2002/0177847 A1 * | 11/2002 | Long | A61B 18/1492 | 606/46 |
| 2002/0179986 A1 * | 12/2002 | Orcutt | B81B 7/007 | 257/417 |
| 2003/0004397 A1 * | 1/2003 | Kameya | A61B 1/05 | 600/101 |
| 2003/0181900 A1 * | 9/2003 | Long | A61B 18/1492 | 606/41 |
| 2003/0181905 A1 * | 9/2003 | Long | A61B 18/1492 | 606/46 |
| 2003/0201462 A1 * | 10/2003 | Pommer | G02B 6/4201 | 257/200 |
| 2003/0216727 A1 * | 11/2003 | Long | A61B 18/1492 | 606/41 |
| 2004/0196392 A1 * | 10/2004 | Yahagi | H04N 5/3572 | 348/241 |
| 2005/0020877 A1 * | 1/2005 | Ishihara | A61B 1/0008 | 600/109 |
| 2005/0075538 A1 * | 4/2005 | Banik | A61B 1/00071 | 600/141 |
| 2005/0118874 A1 * | 6/2005 | Lin | H05K 9/0066 | 439/620.1 |
| 2005/0154262 A1 * | 7/2005 | Banik | A61B 1/00059 | 600/179 |
| 2005/0182291 A1 * | 8/2005 | Hirata | A61B 1/00096 | 600/101 |
| 2005/0205136 A1 * | 9/2005 | Freeman | A01K 11/006 | 137/554 |
| 2005/0243169 A1 * | 11/2005 | Ono | H04N 7/183 | 348/65 |
| 2005/0244095 A1 * | 11/2005 | Ellison | G02B 6/4246 | 385/14 |
| 2006/0063976 A1 * | 3/2006 | Aizenfeld | A61B 1/00096 | 600/179 |
| 2006/0189844 A1 * | 8/2006 | Tien | A61B 1/00103 | 600/143 |
| 2006/0261263 A1 * | 11/2006 | Ishihara | A61B 1/0008 | 250/234 |
| 2007/0057155 A1 * | 3/2007 | Mabuchi | H01L 27/14609 | 250/208.1 |
| 2007/0057156 A1 * | 3/2007 | Mabuchi | H01L 27/14609 | 250/208.1 |
| 2007/0091170 A1 * | 4/2007 | Ota | A61B 1/00045 | 348/65 |
| 2007/0182812 A1 * | 8/2007 | Ritchey | H04N 5/2254 | 348/36 |
| 2007/0211839 A1 * | 9/2007 | Suda | H04N 5/335 | 375/354 |
| 2007/0250006 A1 * | 10/2007 | Court | A61B 5/064 | 604/117 |
| 2008/0068453 A1 * | 3/2008 | Mori | A61B 1/041 | 348/65 |
| 2008/0091065 A1 * | 4/2008 | Oshima | A61B 1/045 | 600/109 |
| 2008/0167523 A1 * | 7/2008 | Uchiyama | A61B 1/00036 | 600/114 |
| 2008/0191347 A1 * | 8/2008 | Sawa | C08G 59/4207 | 257/737 |
| 2008/0208006 A1 * | 8/2008 | Farr | A61B 1/0607 | 600/178 |

FOREIGN PATENT DOCUMENTS

| | | |
|---|---|---|
| EP | 1455216 A1 | 9/2004 |
| JP | 10179516 A | 7/1998 |
| JP | 11137512 A | 5/1999 |
| JP | 2000023911 A | 1/2000 |

* cited by examiner

CAVITY EXPLORATION WITH AN IMAGE SENSOR

BACKGROUND

Technical Field

This disclosure relates to the exploration of cavities, more specifically the exploration of cavities of small dimensions containing areas not directly visible to the naked eye.

Description of the Related Art

Such an exploration can occur with the assistance of an instrument comprising an optical system and a light source to provide images of the area in question. Such an instrument may include an endoscope.

It conventionally comprises a head, or exploration head, which corresponds to the part intended to be introduced into a cavity to be explored and to provide data from this cavity to an outside module intended for managing the interface with a user of the exploration device to provide the user with images of the cavity.

A known exploration device consists of a plurality of optical fibers intended to be introduced into the cavity to be explored, where it will send optical signals from the explored area to a module which is intended to remain outside the cavity. In this context, the outside module comprises an image sensor which is responsible for capturing the optical signals transmitted by the optical fibers. In such an architecture, the optical signals transmitted from inside the cavity to outside the cavity are therefore processed outside the cavity, in the image sensor found in the outside module.

Note that such an exploration device has a significant cost because of the presence of the optical fibers connecting the exploration head to the image sensor. Therefore this device cannot reasonably be a disposable device discarded after one use.

Because of this, the equipment must be disinfected, or at least the optical fibers, between two subsequent uses of the exploration device, with each disinfection presenting an equally significant cost.

In addition, the transmission of optical signals by the optical fibers to the image sensor located in the outside module can degrade the quality of the images obtained in the outside module.

Also known is an exploration device as described in the document U.S. Pat. No. 6,939,295, in the form of a capsule adapted for introduction into the cavity to be explored. Such a capsule comprises a CMOS sensor coupled to a radio transmission unit able to send to the outside the information captured inside the cavity to be explored, providing images of the cavity to the user. For the CMOS sensor to be small in size, a flexible support is used for the integrated circuit. Such an architecture is based on a technology which induces a significant cost in the manufacture of such an exploration device.

Document EP 1 400 214 also describes a cavity exploration device, comprising an exploration part intended to be introduced into the cavity to be explored and comprising a CMOS (Complementary Metal Oxide Semiconductor) image sensor. A dedicated housing for this image sensor is provided in the exploration part. In such an architecture, the integrated circuit comprising the CMOS image sensor as well as the connections between it and an outside module occupy space in the exploration part. Conventionally, when connecting a wire to a conducting pad of an integrated circuit support via a mechanical connection, male and female connectors are used so that the connection has significant mechanical strength. One of these connectors is soldered to the integrated circuit, and the other connector is crimped to the wire. Then the wire, or micro-cable, is connected to the integrated circuit by the connection between the male and female connectors. However, such a connection occupies a relatively significant amount of space, and therefore accommodating the integrated circuit requires a significant amount of space.

Saving space, however, is an important factor in the exploration of cavities of small size.

BRIEF SUMMARY

This disclosure is directed to methods, devices and systems to improve the situation.

A first aspect of the disclosure proposes a process for manufacturing a head of a cavity exploration device, with this head comprising an integrated circuit support having first and second surfaces and a plurality of through-holes associated with respective first and second conducting pads respectively positioned on the first and second surfaces of the integrated circuit.

In an embodiment, the process comprises the following steps to be executed for the holes in the integrated circuit support:

/a/ positioning a conducting micro-cable in the through-hole, with this micro-cable having a portion which is uninsulated for a length greater than or equal to the thickness of the support, /b/ soldering the micro-cable to the associated first and second conducting pads, /c/ gluing the micro-cable with glue to the associated first and second conducting pads, and /d/ molding the micro-cable in first and second layers of resin onto the respective first and second conducting pads, with these resin layers covering the uninsulated portion of the micro-cable.

These measures facilitate creating resistant mechanical connections while manipulating an integrated circuit and micro-cables of very small dimensions.

In this context, "micro-cable" is understood to mean a thin cable, or wire, of a relatively reduced diameter. One can use, for example, a micro-cable of AWG 36 (American Wire Gage). Such a micro-cable can have a diameter which is substantially equal to 0.15 mm. In this manner one can obtain a head of an exploration device which is equipped with an image sensor, for example a CMOS sensor, realized on the integrated circuit support and which can be introduced into small cavities while connected to the outside by micro-cables.

By following the steps described above in an embodiment in the invention, it is no longer required to create mechanical connections, as previously described, via male and female connectors which occupy space and therefore do not allow obtaining an integrated circuit of small size.

By obtaining an integrated circuit of small dimensions according to an embodiment of the invention, it also is no longer required to use a flexible integrated circuit support of the type used in the capsule of document U.S. Pat. No. 6,939,295, of such significant cost. In an embodiment, the reduction in size of the integrated circuit and of its mechanical connections is obtained by the use of connections as described here.

In addition, by directly introducing the sensor into the cavity to be explored, optical fibers are no longer required. Such a characteristic reduces the cost of an endoscopic exploration device and allows discarding after a single use the part intended for introduction into the cavity to be explored. This characteristic eliminates the cost of disinfecting this device, which can be very high, while guaranteeing a good image quality.

In addition, the integrated circuit support can accept an integrated circuit comprising an image sensor which can directly capture the images of the cavity to be explored. The optical signals are therefore not transmitted via optical fibers. This direct image capture allows better image quality.

The arrangement of mechanical connections of the integrated circuit support facilitates using a CMOS image sensor, which is lower in cost than a CCD (Charge Coupled Device) image sensor for example. In fact, a CCD image sensor may be smaller in size than a CMOS sensor, and therefore the utilization of a CCD image sensor may allow more easily obtaining an integrated circuit of small size. But utilization of CCD sensor technology results in a higher cost than that of CMOS sensors. On the other hand, the use of CMOS technology is less expensive, which facilitate using a disposable exploration head.

In an embodiment, such connections free up space on the integrated circuit support next to the image sensor, such that it is advantageously possible to provide a place for a light source such as a light-emitting diode.

In an embodiment, the integrated circuit can comprise at least one light-emitting diode and thus enable exploration of the cavity while illuminating the area for which the user desires to obtain images.

As the micro-cable connections on the integrated circuit allow saving space on the integrated circuit support, it can also be advantageous if the support, in one embodiment, has a hole adapted to receive a tool for performing operations in the cavity and/or a hole adapted to receive a tube for carrying water.

It can be advantageous for the integrated circuit support to have a rounded shape, such as a circle, to allow a pertinent distribution of the image sensor, light sources and holes intended to receive the water tube and the tools.

In one embodiment, the head has first and second exploration surfaces and comprises another integrated circuit support by applying steps /a/-/d/, said integrated circuit supports comprising respectively a first and a second image sensor;

said process comprising the following steps:
  placing the integrated circuit support of said first image sensor on the first exploration surface adapted to capture images of a first region of the cavity,
  placing the integrated circuit support of said second image sensor on the second exploration surface adapted to capture images of a second region of the cavity,
  said first and second regions of the cavity being distinct from each other.

These arrangements facilitate capturing images simultaneously in two different zones of the cavity being explored. The user may avoid the problem of the orientation of the exploration head, particularly when exploring a very narrow cavity as discussed above for an exploration head with a single image sensor.

In addition, the user may view images of two separate zones in the cavity simultaneously, one serving to orient the user when displacing the head within the cavity, and the other serving to guide the user's tools, if applicable, inside an area where an operation is to be performed.

The two image sensors can be connected to an outside terminal, or interface device, such that the images captured by these two image sensors are transmitted from the exploration head to this terminal. The user can then view simultaneously, for example in two windows displayed on the screen of the terminal, the stream of images captured in the first region of the cavity and the stream of images captured in the second region of the cavity.

Thus the user can move the exploration head by referring to the images displayed in one of the windows and can perform operations in the region of the cavity concerned by the images displayed in the other window.

The first exploration surface of the head of the exploration device can correspond to a lateral surface of said head and the second exploration surface can correspond to a front surface of said head.

A second aspect of an embodiment proposes a head of a cavity exploration device, with said head comprising an integrated circuit support presenting first and second surfaces and a plurality of through-holes associated with respective first and second conducting pads respectively placed on the first and second surfaces of the integrated circuit support, wherein the through-holes traversing said integrated circuit support have corresponding micro-cables presenting a portion which is uninsulated. The uninsulated portion may have a length, for example, greater than or equal to the thickness of said support, with said micro-cables being soldered and glued to the first and second associated conducting pads, and being molded in first and second resin layers onto the respective first and second conducting pads, with said resin layers covering the exposed uninsulated portion of said micro-cable.

In one embodiment, the head has first and second exploration surfaces, and comprises another integrated circuit support;

said integrated circuit supports comprising a first and a second image sensor respectively;

said first image sensor being placed on the first exploration surface and adapted to capture images of a first region of the cavity, said second image sensor being placed on the second exploration surface and adapted to capture images of a second region of the cavity, with said first and second regions of the cavity being distinct from each other.

The first exploration surface can correspond to a lateral surface of said head of the exploration device and the second exploration surface can correspond to a front surface of said head.

A third aspect of the disclosure proposes a cavity exploration device comprising:
  a head of a cavity exploration device, with said head being equipped with micro-cables by following a manufacturing process according to the first aspect of the disclosure, and with said head comprising at least an image sensor, and
  an interface module adapted to provide images captured by said image sensor, with said interface module being coupled to the head of the exploration device by said micro-cables.

The head may have an additional hole adapted to receive a water tube, and an additional hole adapted to receive a tool for performing operations in the cavity.

In one embodiment, a process for manufacturing a head of a cavity exploration device, the head including an integrated circuit support presenting first and second surfaces, and a plurality of through-holes associated with respective first and second conducting pads respectively placed on the first and second surfaces of the integrated circuit support, comprises the following steps: positioning respective conducting micro-cables in the through-holes, the micro-cables having an uninsulated portion of a length greater than or equal to a thickness of the support; soldering the micro-cables onto the first and second associated conducting pads; gluing the micro-cables with a glue onto the first and second associated conducting pads; and molding the micro-cable in first and second layers of resin onto the respective first and second conducting pads, with said resin layers covering the uninsulated portion of said micro-cable. In one embodiment, the integrated circuit support comprises an image sensor. In one embodiment, the image sensor is a CMOS sensor. In one embodiment, the integrated circuit support comprises at least one light-emitting diode. In one embodiment, the integrated circuit support has a hole adapted to receive a tool for performing operations in the cavity. In one embodiment, the integrated circuit support has a hole adapted to receive a tube for carrying water.

In one embodiment, a head of a cavity exploration device comprises: an integrated circuit support which has first and second surfaces and a plurality of through-holes associated with corresponding first and second conducting pads respectively placed on the first and second surfaces of the integrated circuit support; and a plurality of corresponding micro-cables, the micro-cables having a portion which is uninsulated for a length greater than or equal to a thickness of the support, soldered and glued to the first and second associated conducting pads, and molded in first and second layers of resin onto the respective first and second conducting pads, with said resin layers covering the uninsulated portion of said micro-cable. In one embodiment, the head further comprises an image sensor coupled to the integrated circuit support. In one embodiment, the head further comprises a light-emitting diode coupled to the integrated circuit support.

In one embodiment, a method of manufacturing a cavity exploration device comprises: forming a plurality of through-holes in an integrated circuit, each through-hole associated with a respective conductive pad on a surface of the integrated circuit; mounting an image sensor on the integrated circuit; and for each of a corresponding plurality of insulated micro-cables, positioning the micro-cable in a corresponding through-hole in the plurality of through-holes such that an uninsulated portion of the micro-cable aligns with the respective conductive pad; soldering the uninsulated portion of the micro-cable to the respective conductive pad to form a solder joint; gluing the micro-cable to the integrated circuit; and covering exposed portions of the solder joint and uninsulated portions of the micro-cable with a resin. In one embodiment, the method further comprises mounting a light emitting diode on the integrated circuit. In one embodiment, each through-hole in the plurality of through-holes is associated with a second respective conductive pad on a second surface of the integrated circuit; positioning the micro-cable in the corresponding through-hole comprises positioning the micro-cable such that the uninsulated portion aligns with both respective conductive pads; and soldering the uninsulated portion of the micro-cable comprises soldering the uninsulated portion of the micro-cable to both respective conductive pads.

In one embodiment, a system to explore cavities comprises: an integrated circuit support having a plurality of through-holes; an image sensor coupled to the integrated circuit support; a plurality of pairs of bonding pads associated with respective through-holes in the plurality of through-holes; a plurality of micro-cables passing through respective through-holes in the plurality of through-holes, each micro-cable in the plurality of micro-cables soldered and glued to a respective pair of bonding pads of the plurality of bonding pads to form respective solder joints; a first layer of resin on a first side of the integrated circuit support configured to cover the solder joints and uninsulated portions of the plurality of micro-cables adjacent to the solder joints on the first side of the integrated circuit support; and a second layer of resin on a second side of the integrated circuit support configured to cover the solder joints and exposed uninsulated portions of the plurality of micro-cables adjacent to the solder joints on the second side of the integrated circuit support. In one embodiment, the system further comprises an interface module coupled to the plurality of micro-cables. In one embodiment, the system further comprising a light-emitting diode coupled to the integrated circuit support. In one embodiment, the system further comprises a guide-hole through the integrated circuit support. In one embodiment, the guide-hole is configured to couple to a tube. In one embodiment, the guide-hole is configured to couple to a tool.

In one embodiment, a system comprises: an integrated circuit support having a plurality of through-holes; an image sensor coupled to the integrated circuit support; a light-emitting diode coupled to the integrated circuit support; a plurality of pairs of bonding pads associated with respective through-holes in the plurality of through-holes; a plurality of micro-cables passing through respective through-holes in the plurality of through-holes, each micro-cable in the plurality of micro-cables soldered and glued to a respective pair of bonding pads of the plurality of bonding pads to form respective solder joints; a first layer of resin on a first side of the integrated circuit support configured to cover exposed electrically conductive surfaces adjacent to the solder joints on the first side of the integrated circuit support; and a second layer of resin on a second side of the integrated circuit support configured to cover electrically conductive surfaces adjacent to the solder joints on the second side of the integrated circuit support. In one embodiment, the first layer of resin is configured to cover an exposed portion of the uninsulated portion of a micro-cable in the plurality of micro-cables. In one embodiment, the first layer of resin is configured to cover an exposed portion of a solder joint. In one embodiment, the system is an endoscope. In one embodiment, the endoscope further comprises: an interface module coupled to the plurality of micro-cables.

Other features, goals, and advantages of embodiments will become clear upon reading the description.

BRIEF DESCRIPTION OF THE SEVERAL
VIEWS OF THE DRAWING(S)

Embodiments of the invention will also be better understood by referring to the drawings, in which:

FIGS. 2-A and 2-B respectively illustrate a front view and a back view of a head of an exploration device according to one embodiment;

DETAILED DESCRIPTION

Figure 1:
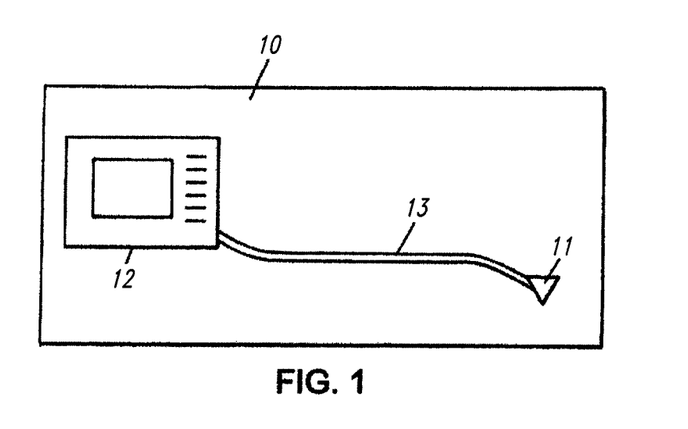
FIG. 1 illustrates an exploration device according to one embodiment.

FIG. 1 illustrates an exploration device 10 according to one embodiment.

Such a device can advantageously be used for the exploration of any cavity which is not directly visible to the human eye, particularly cavities which are relatively narrow and difficult to access, as this exploration device has a head of small dimensions.

The domain for such an exploration device is broad. For example, it is equally useful in fields such as medicine, avionics, aeronautics, etc.

In addition, this head comprising an image sensor facilitates providing images of good quality to the user of the exploration device.

The device 10 comprises a head 11 for exploring a cavity, which is connected to an interface module 12 via micro-cables 13. In one embodiment, this head comprises a CMOS image sensor.

Embodiments may employ any interface module. The interface module is adapted to receive data concerning the images captured by the exploration head, more specifically by the image sensor, and to process them so as to provide them in a usable form to the user of the exploration device. The interface module may be a computer, for example.

Figure 2A:
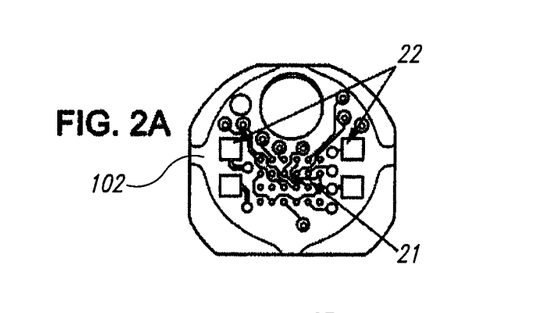
Figure 2B:
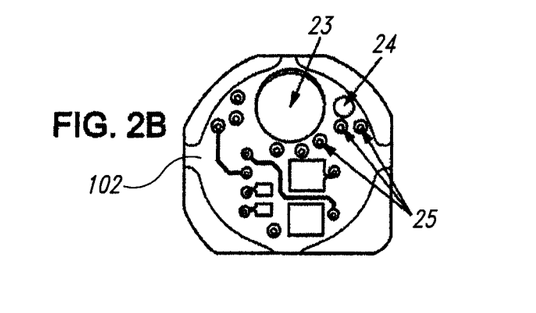

FIGS. 2-A and 2-B respectively illustrate a front view and a back view of a head of an exploration device according to one embodiment. Note that the micro-cable connections according to an embodiment advantageously allow using the integrated circuit support 102 supporting the CMOS image sensor (see FIG. 3) to introduce at least one light source 22 as well as guides for a tube carrying water from outside the cavity to inside the cavity and for a tube corresponding to a tool for performing operations in the cavity. Such guides correspond, in this example, to a first and a second hole 23, 24.

FIG. 2-A illustrates the integrated circuit support comprising a CMOS image sensor 21 and two light-emitting diodes 22.

FIG. 2-B illustrates a through-hole 23 in the integrated circuit support, for receiving a tool (not shown) for performing operations in the cavity to be explored. Thus, the user of the exploration device is able to perform certain operations in the cavity being explored. Another through-hole 24, adapted to receive a tube for carrying water (not shown), is also provided in the integrated circuit support. The integrated circuit support has conducting pads 25.

One should note that the process for manufacturing the exploration head according to an embodiment saves space, which facilitates placing holes directly in the integrated circuit support 102. In particular, said holes can be adapted to bring water into the cavity and to receive a tool for performing operations in the cavity.

Figure 3:
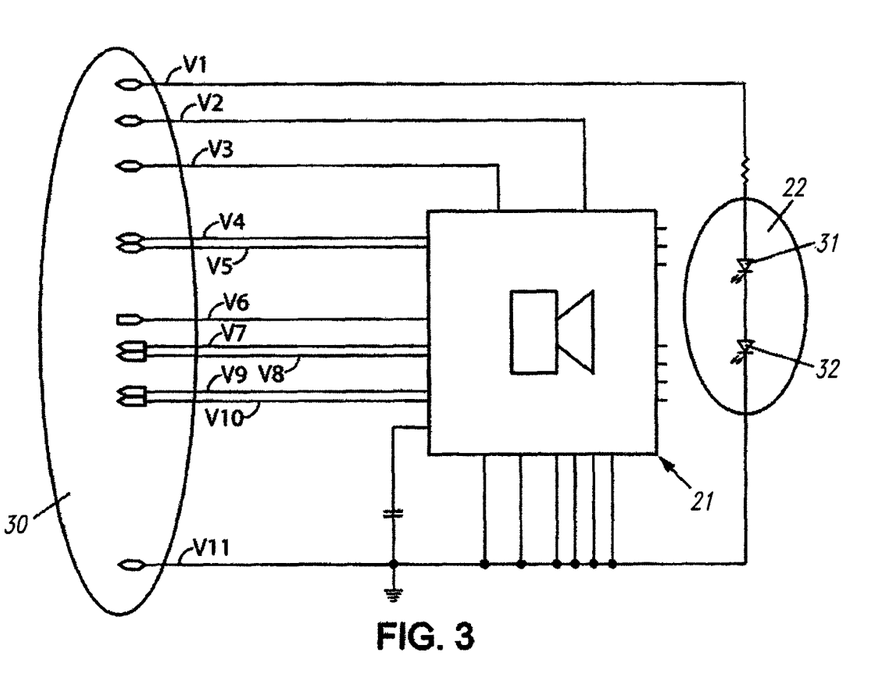
FIG. 3 illustrates an integrated circuit of a head of an exploration device according to one embodiment in a first and a second case.

FIG. 3 provides a detailed illustration of the integrated circuit comprised in the exploration head according to an embodiment.

This integrated circuit comprises two light-emitting diodes 22, respectively labeled 31, 32. It also comprises a CMOS image sensor 21. The inputs and outputs of these elements, the light-emitting diodes and image sensor, are connected via micro-cables to the interface module 12.

Embodiments may employ any source of power. For example, power may be provided to the electronic components of the head 11 via the interface module. However, it is easy to provide for other configurations. For example, power may be provided via micro-cables 13, by a module other than the interface module, or by an energy storage or generating device (not shown) on the head 11.

A zone of micro-cable connections 30 is illustrated in FIG. 3. In this embodiment, the micro-cables are respectively connected to:
  the power signal for the lighting V1,
  the power signals for the CMOS sensor V2 and V3,
  the control signals for the CMOS sensor V4 and V5, with these signals possibly using the I$^2$C standard (Inter Integrated Circuit Bus),
  the clock signal for the CMOS sensor V6,
  the video stream transfer signals V7, V8, V9 and V10, with these signals possibly using the SubLVDS standard (Sub Low Voltage Differential Signaling),
  the ground signal V1.

Figure 4:
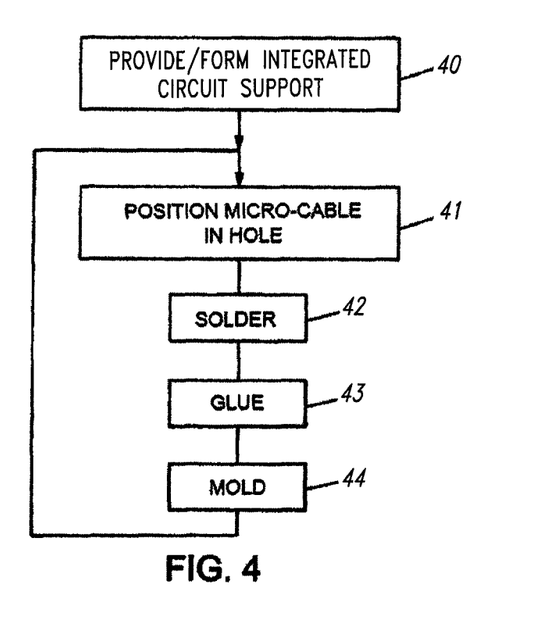
FIG. 4 illustrates steps of a process for manufacturing a head of an exploration device according to one embodiment.

FIG. 4 illustrates steps in the manufacturing process for the head of an exploration device according to an embodiment.

A support for an integrated circuit is provided or formed at step 40. Such a support may be round in shape.

On this support is integrated a CMOS image sensor and two light-emitting diodes. This integrated circuit support has a set of conducting pads placed in pairs on the integrated circuit, with these pairs positioned on either side of the support. Respective through-holes traversing the integrated circuit support pass through the pairs of conducting pads.

These pairs of conducting pads correspond to the inputs/outputs of the components, such as those listed above with reference to the connection zone 30. They are configured to couple to the interface module, or at least to a module separate from the head, such as a module outside the cavity configured to receive data regarding the images captured by the image sensor of the exploration head.

Figure 5:
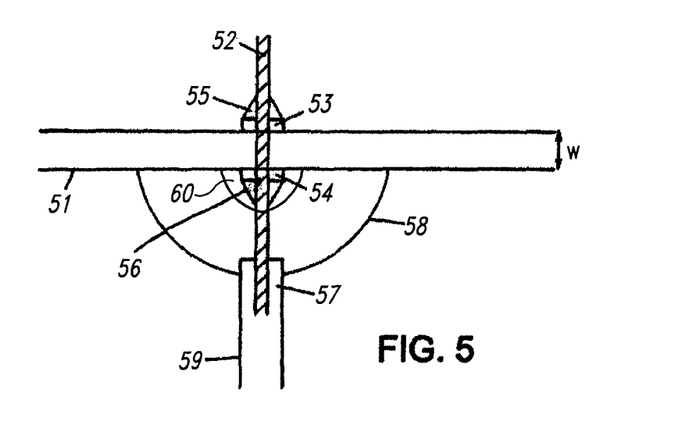
FIG. 5 illustrates a connection of a micro-cable with the integrated circuit support in a head manufactured according to an embodiment.

FIG. 5 illustrates a connection made according to one embodiment. A micro-cable 59 which comprises a sheath 57 and one or more wires 52 is configured to couple the head to the interface module. Any type of micro-cable may be used. For example, one can advantageously use a micro-cable which has a diameter of 0.3 mm.

The micro-cable is bare of insulation for a length which is greater than or equal to the width, labeled w, of the integrated circuit support 51. Then in a step 41, the micro-cable is placed in the corresponding through-hole which traverses the integrated circuit support 51 at the location of a pair of conducting pads 53 and 54, such that its uninsulated portion is aligned with the width of the support 51 and allows the wire 52 to come in contact with the two conducting pads 53 and 54.

Then, in a step 42, the wire 52 is bonded with solder 55 to the pad 53 on the upper surface of the integrated circuit support, and is bonded with solder 56 to the pad 54 on the lower surface of the integrated circuit support.

Next, in a step 43, this wire is also glued at the two conducting pads 53 and 54 by means of a glue 60, which can be resin-based.

Next, in a step 44, the connection is consolidated by means of a resin-based molding 58 which is placed at the conducting pads 53 and 54 such that it covers the previously applied soldering and glue, as well as covering any exposed uninsulated portion of the micro-cable 59. To improve the strength of a connection, the molding may also cover a portion of the sheath 57 of the micro-cable, as illustrated in FIG. 5.

As such connections may be reduced in size, the facilitate room for light-emitting diodes on the integrated circuit, as well as holes through the integrated circuit support. For example, there can be a hole for the water tube and a hole for a tool.

Figure 6:
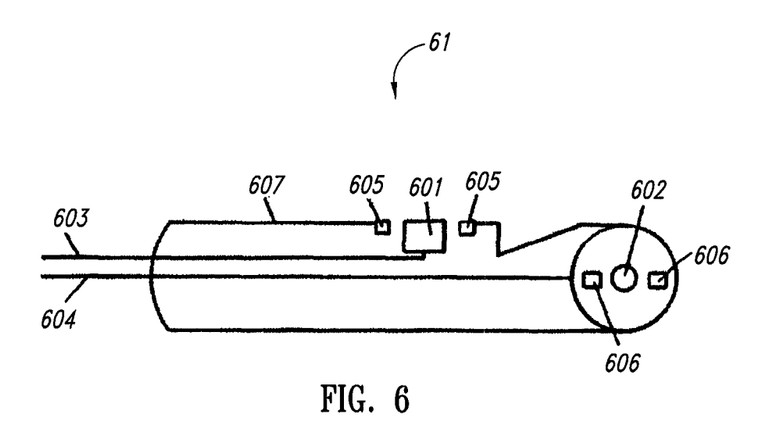
FIG. 6 illustrates a head of an exploration device according to an embodiment of the invention.

FIG. 6 illustrates a head 61 of an exploration device according to an embodiment. This head comprises first and second image sensors 601, 602 of type CMOS (Complementary Metal Oxide Semiconductor). The first sensor 601 is positioned on a lateral surface 701 of the exploration head 61, while the second image sensor is positioned on a front surface of the exploration head 61. In such a configuration, the two image sensors of the head are able to capture images of two completely separate zones of the cavity being explored. These first and second image sensors are connected to a terminal by respective cables 603 and 604, through which the data concerning the two image sensors are transmitted to the outside terminal. Various architectures can be used to couple the image sensors and the terminal. For example, there can be intermediate devices between the exploration head 61 and the outside terminal, which could be handle the processing of the two streams of images coming from the two respective image sensors. In addition, in an embodiment, the exploration head 61 can be equipped with light sources, so as to illuminate the regions of the cavity respectively targeted by the two image sensors 601 and 602. As illustrated, there are two first light sources 605, positioned on opposite sides of the first image sensor 601 on the lateral surface of the head, as well as two second light sources 606, positioned on opposite sides of the second image sensor 602 on a front surface of the head 61.

Figure 7:
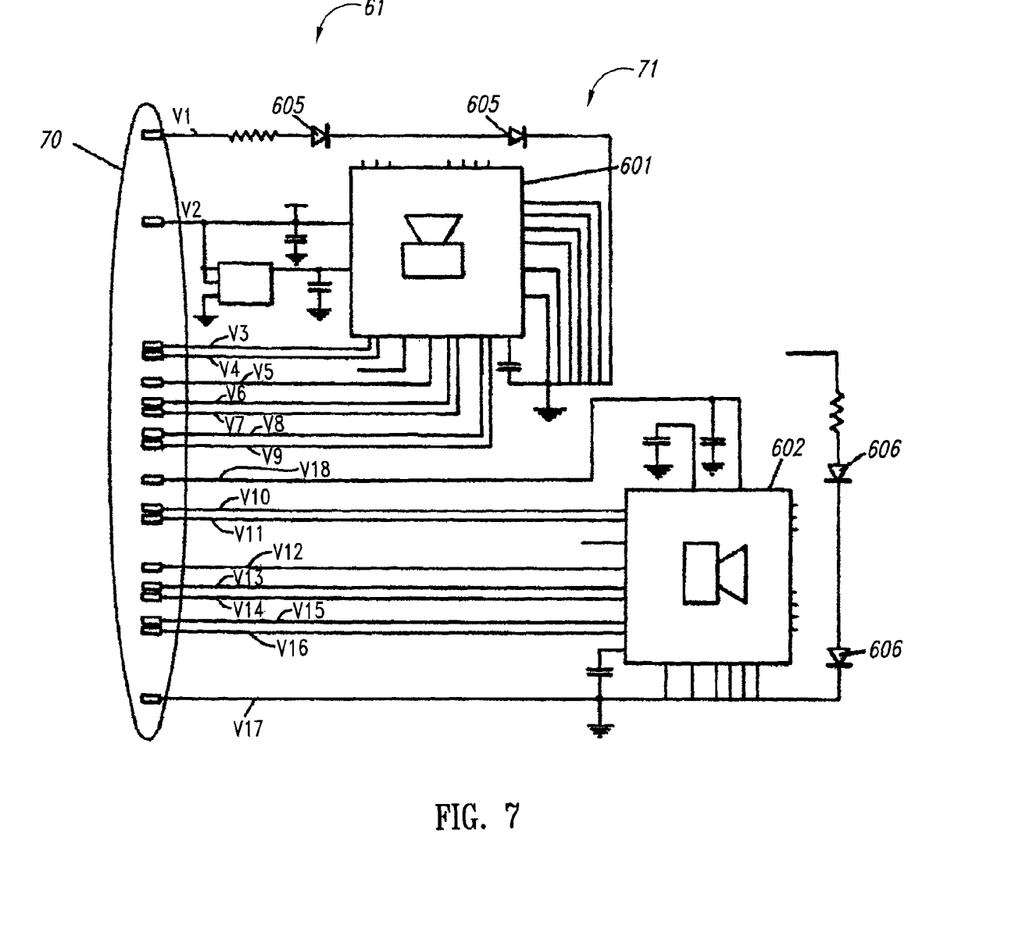
FIG. 7 illustrates an integrated circuit of a head of an exploration device according to an embodiment of the invention.

FIG. 7 illustrates an integrated circuit 71 of an exploration head 61 of an exploration device according to an embodiment. This integrated circuit comprises the two light-emitting diodes 605 and the two light-emitting diodes 606. It also comprises the first CMOS image sensor 601 and the second image sensor 602. The inputs and outputs of these elements, light-emitting diodes and image sensors, are connected via micro-cables to the interface module via a connection zone 70.

In this context, power is provided to the electronic components of the head 61 via the interface module. However, it is easy to allow for other configurations where the power is provided via other connections, such as the connection 603 (See FIG. 6), which can correspond to micro-cables 603, by a module other than the interface module. No limitation is placed on the present invention regarding this aspect. As illustrated in FIG. 7, cables couple the first image sensor 601 to:

the power signal for the light sources V1,
the power signal for the CMOS image sensor V2,
the control signals for the CMOS image sensor V3 and V4, with these signals possibly using the I²C standard (Inter Integrated Circuit Bus),
the clock signal for the CMOS image sensor V5,
the video stream transfer signals V6, V7, V8 and V9, with these signals possibly using the SubLVDS standard (Sub Low Voltage Differential Signaling),
and the second image sensor 602 to:
the power signal for the CMOS image sensor V18,
the control signals for the CMOS image sensor V10 and V11, with these signals possibly using the I²C standard (Inter Integrated Circuit Bus),
the clock signal for the CMOS image sensor V12,
the video stream transfer signals V13, V14, V15 and V16, with these signals possibly using the SubLVDS standard (Sub Low Voltage Differential Signaling),
the ground signal V17.

In one embodiment, the wiring connecting the head of the exploration device to the outside terminal corresponds to micro-cables. Using such micro-cables and by implementing mechanical connections of these micro-cables to an integrated circuit support intended to receive the image sensors facilitates optimizing the space occupied in the exploration head by the electronic components and their connections. Under these conditions, it is possible to have an exploration head which is small in size, while still being equipped with two image sensors, such as CMOS sensors, which can be introduced into small cavities while connected to the outside via micro-cables.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process, comprising:
manufacturing a head of a cavity exploration device, the head including an integrated circuit support presenting first and second surfaces, and a plurality of through-holes associated with respective first and second conducting pads respectively placed on the first and second surfaces of the integrated circuit support, by:
positioning respective conducting micro-cables in the through-holes, the micro-cables having an uninsulated portion of a length greater than or equal to a thickness of the support;
soldering the micro-cables onto the first and second associated conducting pads;
gluing the micro-cables with a glue onto the first and second associated conducting pads; and
molding the micro-cable in first and second layers of resin onto the respective first and second conducting pads, with said resin layers covering the uninsulated portion of said micro-cable.

2. The process for manufacturing a head according to claim 1 wherein the integrated circuit support comprises an image sensor.

3. The process for manufacturing a head according to claim 2 wherein the image sensor is a CMOS sensor.

4. The process for manufacturing a head according to claim 1 wherein the integrated circuit support comprises at least one light-emitting diode.

5. The process for manufacturing a head according to claim 1 wherein the integrated circuit support has a hole adapted to receive a tool for performing operations in the cavity.

6. The process for manufacturing a head according to claim 1 wherein the integrated circuit support has a hole adapted to receive a tube for carrying water.

7. The process of claim 2 wherein the head comprises first and second exploratory surfaces, the integrated circuit support is a first integrated circuit support and the image sensor is a first image sensor, the process further comprising:

configuring the first integrated circuit support to position the first image sensor on the first exploratory surface of the head to capture images of a first region of the cavity;

providing a second integrated circuit support in the head, the second integrated circuit support having a second image sensor, and presenting first and second surfaces, and a plurality of through-holes associated with respective first and second conducting pads respectively placed on the first and second surfaces of the second integrated circuit support:

positioning respective conducting micro-cables in the through-holes of the second integrated circuit support, the micro-cables having an uninsulated portion of a length greater than or equal to a thickness of the second integrated circuit support;

soldering the micro-cables positioned in the through-holes of the second integrated circuit support onto the first and second associated conducting pads;

gluing the micro-cables positioned in the through-holes of the second integrated circuit with glue onto the first and second associated conducting pads;

molding the micro-cable in first and second layers of resin onto the respective first and second conducting pads of the second integrated circuit support, with the resin layers covering the uninsulated portion of the respective micro-cables; and configuring the second integrated circuit support to position the second image sensor on the second exploratory surface of the head to capture images of a second region of the cavity, distinct from the first region of the cavity.

8. A head of a cavity exploration device, comprising:

an integrated circuit support which has first and second surfaces and a plurality of through-holes associated with corresponding first and second conducting pads respectively placed on the first and second surfaces of the integrated circuit support; and a plurality of corresponding micro-cables, the micro-cables having a portion which is uninsulated for a length greater than or equal to a thickness of the support, soldered and glued to the first and second associated conducting pads, and molded in first and second layers of resin onto the respective first and second conducting pads, with said resin layers covering the uninsulated portion of the micro-cables.

9. The head of claim 8, further comprising an image sensor coupled to the integrated circuit support.

10. The head of claim 9, further comprising a light-emitting diode coupled to the integrated circuit support, wherein the image sensor is an image sensor of an endoscope.

11. The head of claim 8 wherein the integrated circuit support is a first integrated circuit support having a first image sensor configured to capture images of a first region of the cavity, the head further comprising:

a second integrated circuit support which has first and second surfaces and a plurality of through-holes associated with corresponding first and second conducting pads respectively placed on the first and second surfaces of the second integrated circuit support; and a second plurality of corresponding micro-cables having a portion which is uninsulated for a length greater than or equal to a thickness of the second integrated circuit support, soldered and glued to the first and second associated conducting pads of the second integrated circuit support and molded in first and second layers of resin onto the respective first and second conducting pads of the second integrated circuit support, with the resin layers covering the uninsulated portion of the second plurality of microcables, wherein the second integrated circuit support has a second image sensor configured to capture images of a second region of the cavity, the second region being distinct from the first region.

12. The head of claim 11 wherein the first integrated circuit support is configured to support the first image sensor along a lateral surface of the head and the second integrated circuit support is configured to support the second image sensor along a front surface of the head.

* * * * *